(12) United States Patent
Weinstein

(10) Patent No.: US 6,297,288 B1
(45) Date of Patent: *Oct. 2, 2001

(54) METHOD OF PREVENTING THE EFFECTS OF ALTERED Δ-5 PATHWAY STEROIDOGENESIS IN ADRENERGICALLY BLOCKADED CONDITIONS

(76) Inventor: Robert E. Weinstein, 177 Commonwealth Ave., Boston, MA (US) 02116

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/781,828

(22) Filed: Jan. 10, 1997

Related U.S. Application Data

(60) Provisional application No. 60/009,883, filed on Jan. 11, 1996.

(51) Int. Cl.[7] ................................................. A61K 31/135
(52) U.S. Cl. ........................................... 514/653; 514/653
(58) Field of Search ................................... 514/178, 182, 514/653

(56) References Cited

PUBLICATIONS

WPIDSAN 95–366121, Bodmer et al, Oct. 12, 1995.*
WPIDSAN 93–100644 Gluzman et al, Mar. 18, 1993.*
CA 123:350364 Terui et al, Oct. 9, 1995.*
Hall et al, Annals of Rh. Ds, 52: 211–214, 1993.*

* cited by examiner

*Primary Examiner*—Rebecca Cook
(74) *Attorney, Agent, or Firm*—Gregory G. Glover; Ropes & Gray

(57) ABSTRACT

The production of sex steroids by the Δ-5 steroidogenic pathway has been found to be under control of the adrenergic nervous system, and sex steroids produced by this pathway are diminished in individuals with adrenergically-blockaded conditions. This invention relates to diminishing the consequences of suppressed Δ-5 pathway steroidogenesis in individuals with adrenergically blockaded conditions by the administration of compositions which raise the serum levels of sex steroids.

10 Claims, 1 Drawing Sheet

General Scheme/Steroid Synthesis

METHOD OF PREVENTING THE EFFECTS OF ALTERED Δ-5 PATHWAY STEROIDOGENESIS IN ADRENERGICALLY BLOCKADED CONDITIONS

This application claims priority to Ser. No. 60/009,883 filed Jan. 11, 1996.

INTRODUCTION

This invention relates to the recognition that the levels of sex steroids produced by the Δ-5 steroidogenic pathway are diminished in individuals with adrenergically blockaded conditions. This invention also relates to correcting the consequences of alteration of the Δ-5 steroidogenic pathway in individuals with adrenergically blockaded conditions. The invention describes methods for preventing the effects associated with suppressed Δ-5 pathway steroidoenesis by the administration of compositions which raise the serum levels of sex steroids.

BACKGROUND OF THE INVENTION

Allergic rhinitis, atopic dermatitis and asthma are three clinical disorders which are grouped under the name "atopy," a Greek word meaning "altered reactivity." These clinical disorders tend to occur together within a single individual. In addition, these disorders tend to cluster within families, and family members might be affected with one or more manifestations with varying degrees of severity.

According to one hypothesis, the unifying feature which underlies the atopic disorders is an altered reactivity or, more specifically, a lack of responsiveness to adrenergic (adrenalin-like) stimulation. (Szentivanyi A. The beta adrenergic theory of the atopic abnormality in bronchial asthma. J. Allergy 42:203–232, 1968.) Responsiveness to adrenergic stimulation may be measured by the effect of administering an adrenergic stimulant. Adrenergic stimulants are compositions characterized by their ability to produce effects similar to the effects produced by the administration of adrenalin. Adrenergic stimulants include medications such as adrenalin, isoproterenol, and albuteral.

When an adrenergic stimulant is administered to individuals with atopy, the effect on widely divergent organ systems is blunted compared to the effect in non-atopic individuals. For example, when an adrenergic stimulant is administered to atopic individuals, it produces less of a rise in blood sugar, less of an effect on peripheral white blood cells and less of an effect on bronchial smooth muscle than in non-atopic individuals. This condition is referred to as adrenergic blockade. Adrenergically blockaded conditions (AdBCs) include the following: respiratory allergies, skin allergies, and asthma.

A relationship between steroidogenesis and adrenergic blockade, the basic pathophysiologic abnormality associated with atopic disorders, has been previously unrecognized. Researchers, however, have recently found that the diminished adrenergic responsiveness in individuals with AdBCs results in a decrease in steroidogenesis. (Weinstein R E, Lobocki C A, Gravett S, Hum H, Negrich R, Herbst J, Greenberg D, Pieper D R. Decreased adrenal sex steroid levels in the absence of glucocorticoid suppression in postmenopausal women. J All Clin Immunol 97:1–8, 1996.) Serum levels of the sex steroids, dehydroepiandrosterone (DHEA), dehydroepiandrosterone sulfate (DHEAS), and estrogens have been found to be decreased in AdBCs. This finding resulted from a study of asthmatic women, who are representative of subjects with AdBCs in that the bronchial response to adrenalin is found to be altered in these individuals. (Szentivanyi A. The beta adrenergic theory of the atopic abnormality in bronchial asthma. J. Allergy 42:203–232, 1968.) DHEA, DHEAS, and the estrogens, estadiol and estriol, were lower in the women with AdBCs compared to a group of women without AdBCs.

The diminished levels of serum DHEAS in the subjects with asthma can be corrected by the administration of an adrenergic stimulant, albuteral. The mode of action for albuteral is substantially similar to the mode of action for other adrenergic stimulants. Therefore, researchers have concluded that the decrease in DHEA, DHEAS and estrogens results from diminished adrenergic responsiveness which occurs in AdBCs.

The diminished adrenergic responsiveness in individuals with AdBCs is specific to the pathway in which the weak androgen DHEA, DHEAS, and estrogens are formed. See FIG. 1. Some steroids in the Δ-4 steroidogenic pathway were not decreased in subjects with AdBCs. For example, 17-OH progesterone and cortisol were found to be normal. Both 17-OH progesterone and cortisol are produced by a pathway which diverges from the one in which DHEA, DHEAS, estradiol and estriol are produced. This suggests that adrenergic blockade affects only the Δ-5 steroidogenic pathway.

DHEA, DHEAS, and Estrogens

DHEA and its sulfated derivative, DHEAS, are major secretory products of the adrenal gland. (Rosenfield R S, Hellman L, Gallagher T F Metabolism and interconversion of dehydroepiandrosterone and dehydroepiandosterone sulphate. J. Endocrinol Metab 35:178–93, 1972.) Levels decrease with age and low levels have been postulated to be predictive of decreased life expectancy and increased mortality from cardiovascular disease. (Orentrich N, Brind J L, Rizer R L, Vogelman J H. Age changes and sex differences in serum dehydroepiandrosterone sulfate concentrations throughout adulthood. J. Clin. Endocrinol Metab 59:551–5, 1984; Barrett-Connor E B, Khaw K, Yen S S C. A prospective study of DHEAS, mortality, and cardiovascular disease. N Engl J Med 315:1519–24, 1986.) DHEA has also been shown to affect immune function. (Hall G M, Perry L A, Spector T D. Depressed levels of dehydroepiandrosterone sulphate in postmenopausal women with rheumatoid arthritis but no relation with axial bone density. Ann Rheum Dis 52:211–214, 1993; Deighton C M, Watson M J, Walker D J. Sex hormones in postmenopausal BLA-identical rheumatoid arthritis discordant siblings. J. Rheumatology 19(11):1663–7, 1992; Tannen R H A and Schwartz A G. Reduced weight gain and delay of Coombs positive hemolytic anemia in NZB mice treated with dehydroepiandrosterone (DHEA). (Abstr.) Fed. Proc. 41:463, 1982; Lucas J., Ahmed S A, Casey L, MacDonald P C. Prevention of autoantibody formation and prolonged survival in New Zealand Black/New Zealand White F1 mice fed dehydroepiandrosterone. J Clin Invest 75:2091–93, 1985; Daynes R A, Dudley, D J, Araneo B A. Regulation of murine lympholine production in vivo. Dehydroepiandrosterone is a natural enhancer of interleukin 2 synthesis by helper T cells. Eur J Immunol 20:793, 1990; Risdon G, Moore T A, Kumar V. Bennett M. Inhibition of murine killer cell differentiation by dehydroepiandrosterone. Blood 78:2387–9, 1991.) Immune function may become disordered with age and aspects of this immune senescence can be ameliorated experimentally by DHEA. (Weksler M E. Immune senescence and adrenal steroids: immune dysregulation and the action of dehydrepiandrosterone (DHEA) in old animals. European Journal of Clinical Pharmacology. 45 suppl. 1:S21–23, 1993; Daynes R A, Araneo B A, Ershler W B, Maloney C, Li GZ, Ryu S Y.

Altered regulation of IL-6 production with normal aging. Possible linkage to the age-associated decline in dehydroepiandrosterone and its sulfated derivative. J Immunol 195 (12):5219–5230, 1993.)

DHEA, DHEAS, and estrogens also regulate immune function and regulate the elaboration of interleukins which influence the production of allergic antibody, immunoglobin E (IgE). These considerations suggest the benefits of restoring or increasing altered sex steroids in AdBCs.

Decreased levels of DHEA, DHEAS, and estrogens are associated with an increased risk of cardiovascular disease and increased risk of bone loss and osteoporosis. These findings suggest that subjects with severe asthma, especially women, have an increased mortality from ischemic heart disease. (Toren K. Lindholm N B. Do patients with severe asthma run an increased risk from ischemic heart disease? International Journal of Epidemiology 25:617–20, 1996.) These effects can be avoided by supplementation with sex steroids.

Adrenergically Blockaded Conditions

One of the characteristic immune manifestations of adrenergically blockaded conditions (AdBCs) is an overproduction of allergic antibody, immunoglobulin E (IgE). Allergic antibody has the characteristic of attaching to a type of cell located in the skin and in the mucous membranes of the respiratory tract which produces or stores mediators such as histamine. Primed with IgE on their surface, upon exposure to a specific antigen, the agent which the antibody recognizes, these cells release mediators such as histamine and leukotrienes. The release of mediators results in allergic manifestations, (e.g., itching, squeezing and bronchial constriction).

The production of allergic antibody is regulated by interleukins, products of immune cells which regulate the functioning of the cells themselves or the functioning of other immune cells. IgE production is enhanced by interleukin-4 (IL-4) and interleukin-6 (IL-6), and inhibited by another interleukin, gamma-interferon. DHEA experimentally decreases the overproduction of IL-6 in aging and DHEAS enhances production of interleukin-2 (IL-2). (Daynes R A, Araneo B A, Ershler W B, Maloney C, Li GZ, Ryu SY. Altered regulation of IL-6 production with normal aging. Possible linkage to the age-associated decline in dehydroepiandrosterone and its sulfated derivative. (J Immunol 195(12):52:5219–5230 (1993).) IL-2 is known to result in the production of increased gamma-interferon. (Daynes R A, Dudley, D J, Araneo B A. Regulation of murine lymphokine production in vivo. Dehydroepiandrosterone is a natural enhancer of interleukin 2 synthesis by helper T cells. Eur J Immunol 20:793, 1990.) Therefore, finding of diminished levels of DHEA and DHEAS in individuals with atopy consequent to adrenergic blockade provides a link to correcting allergic antibody overproduction in AdBCs by correcting the depletion of DHEA and DHEAS.

Pathogenesis of osteoporosis is multifactorial, factors being activity and weight bearing. Inactivity and use of cortisone-like medication are usually considered factors in osteoporosis related to AdBCs. (Ip M, Lam K, Yam L, Kung A, Ng M. Decreased bone mineral density in premenopausal asthma patients receiving long-term inhaled steroids. Chest 105:1722–7, 1994; Eisman JA. Pathogenesis of Osteoporosis In Rheumatology. Klippel J A, Dieppe P A (eds.) pp. 33.1–33.6, St. Louis, 1994 Mosby.)

We now know that another consideration, adrenergic blockade and diminished hormone synthesis are likely contributing factors. The recent finding that DHEA, DHEAS and estrogens are decreased in AdBCs is likely to be another cause of bone depletion and osteoporosis. Moreover, it is known that depletion of DHEA, DHEAS and estrogens increases bone reabsorption and osteoporosis. These effects can be improved experimentally by DHEA supplementation. (Daynes R A, Araneo B A, Ershler W B, Maloney C, Li GZ, Ryu S Y. Altered regulation of IL-6 production with normal aging. Possible linkage to the age-associated decline in dehydroepiandrosterone and its sulfated derivative. J Immunol 195(12):52:5219–5230, 1993; Jilka R L, Hangoc G I, Girasole G, Passari G, Williams D C, Abrams J S, Boyce B, Broxmeyer H, Manolagas S C. Increased osteoclast development after estrogen loss: Mediation by interleukin-6. Science 257:88–91, 1992.)

DESCRIPTION OF THE INVENTION

This invention relates to correcting the consequences of alteration of the Δ-5 steroidogenic pathway in individuals with adrenergically blockaded conditions. The invention describes methods for preventing the effects associated with suppressed Δ-5 pathway steroidogenesis by the administration of compositions which raise the serum levels of sex steroids.

Figure 1:
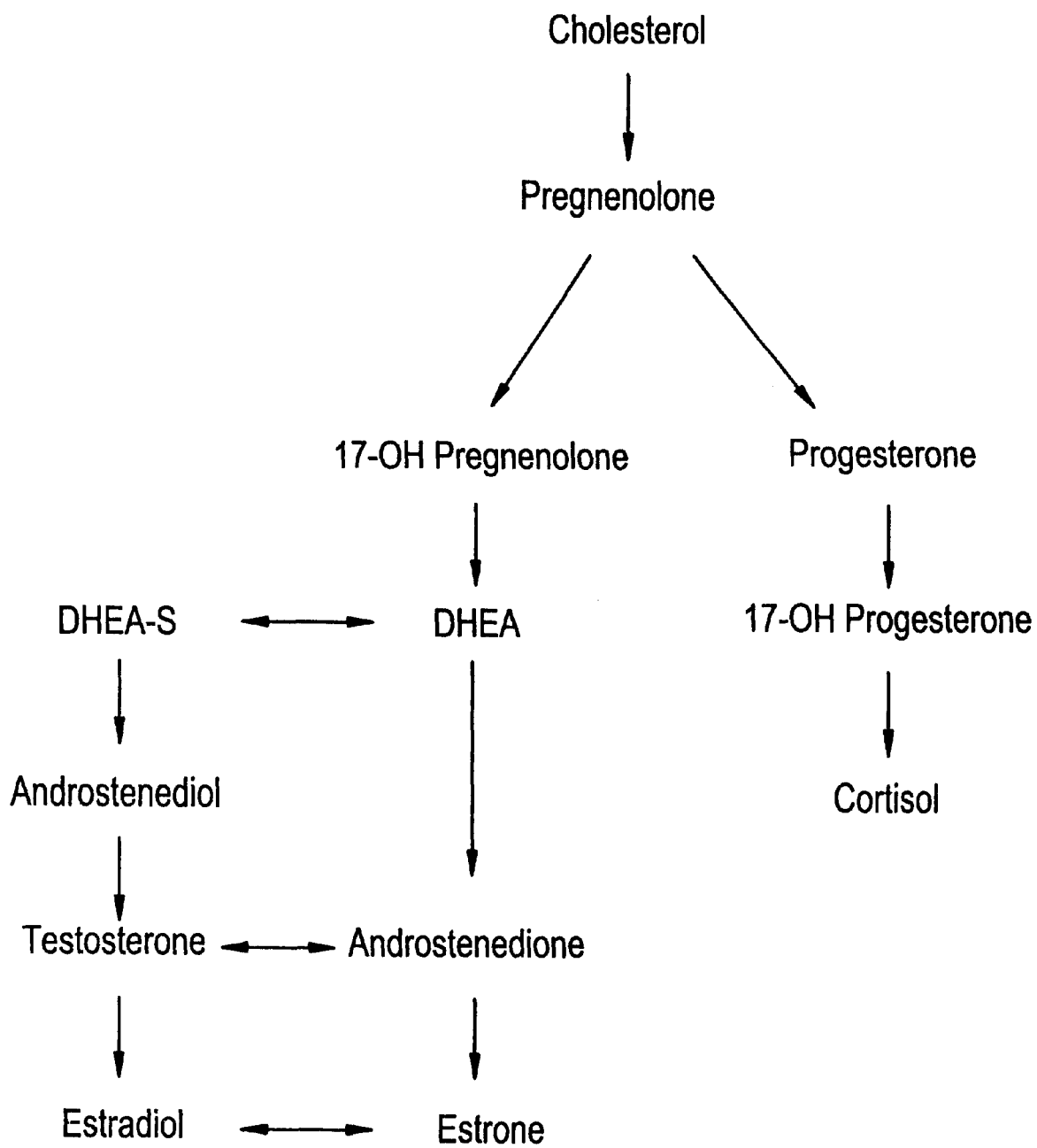
FIG. 1 describe the general scheme of steroid synthesis

Human steroid synthesis proceeds along two major paths: Pregnenolone is converted to DHEA and estrone in one pathway, termed the Δ-5 pathway (in accordance with the position of the double bond in the first ring of the steroid molecule), and pregnenolone is converted to 17-OH progesterone and cortisol in the other, termed the Δ-4 pathway. The Δ5 pathway has been shown to be affected by adrenergic blockade. The Δ-4 pathway is not affected by adrenergic blockade.

DETAILED DESCRIPTION

Treatment to remedy suppressed Δ-5 pathway steroidogenesis in adrenergically blockaded conditions (AdBCs) is suggested in all individuals with AdBCs to prevent or correct alterations in immunologic function including altered allergic antibody formation, and in adults to also diminish the risk of cardiovascular disease and osteoporosis. The remedy of suppressed Δ-5 pathway steroidogenesis may be achieved by adrenergic stimulation, replacement of sex steroids, or administration of medications intended to have the effects of sex steroids.

The compositions may be administered by any route, including oral, parenteral, transdermal, nasal or transmembrane. Transmembrane administration would include topical and inhalation therapies.

Adrenergic Stimulation of the Δ-5 Pathway

The Δ-5 pathway has been shown to be stimulated in AdBCs by adrenergic agonists. Adrenergic stimulation can be achieved clinically as follows:

By the oral route with a commonly used adrenergic stimulant, albuteral sulfate.

Albuterol sulfate 2 mg. to 4 mg. orally two to four times a day in adults and 2 mg. orally two to four times a day in children ages 6–12. For children 2–6 years of age: 0.1 mg/kg orally two to three times a day.

Another route of adrenergic stimulation is by the respiratory route. Suggested regimens in adults and children over 12 years of age include: the following: (a) Albuteral sulfate (Proventil®) 180 mcg. regularly inhaled four times a day and (b) Salmeterol xinafoate (Serevent®) 42 mcg. regularly inhaled twice a day.

Replacement for DHEA

Replacement dosing in AdBCs may vary with the extent of adrenergic blockade. Based upon the use of DHEA as a dietary supplement, replacement for DHEA is achieved by dosing in a range from 25–100 mg. of DHEA per 24 hour period as a single dose in adults of both sexes affected with AdBCs.

Estrogen Replacement

Esterified estrogen tablets such as Estratabs® (Solvay Pharmaceuticals) 0.3 mg. to 1.25 mg. or more daily is administered cyclically. Alternatively, Estrone such as ORTHO-EST® (Ortho Pharmaceuticals) 0.75 to 6 mg. daily is administered cyclically.

What is claimed is:

1. A method of preventing the effects of suppressed $\Delta$-5 pathway steroidogenesis in an individual with adrenergically blockaded conditions comprising the step of administering an effective amount of adrenergic stimulant to said individual.

2. A method to raise the levels of sex steroids produced by the $\Delta$-5 steroidogenic pathway affected by the adrenergic blockade of the $\Delta$-5 steroidogenic pathway in an individual with suppressed $\Delta$-5 pathway steroidogenesis comprising the step of administering an effective amount of adrenergic stimulant to said individual.

3. A method according to claim 2, wherein the sex steroid is DHEA.

4. A method according to claim 2, wherein the sex steroid is DHEAS.

5. A method according to claim 2, wherein the sex steroid is an estrogen.

6. A method according to claim 1, wherein the adrenergic stimulant is $\beta$-agonist.

7. A method according to claim 2, wherein the adrenergic stimulant is a $\beta$-agonist.

8. A method according to claim 6 or claim 7, wherein the $\beta$-agonist is albuteral.

9. A method according to claim 6 or claim 7, wherein the $\beta$-agonist is albuteral administered via the respiratory route.

10. A method according to claim 6 or claim 7, wherein the $\Delta$-5 agonist is salmeterol xinafoate administered via the respiratory route.

* * * * *